United States Patent [19]

Voges

[11] Patent Number: 4,475,907
[45] Date of Patent: Oct. 9, 1984

[54] BODY SECRETION COLLECTING DEVICE WITH IMPROVED LIQUID CONDUIT CONNECTION BETWEEN CONTAINER AND HOLDER

[75] Inventor: Karl-Friedrich Voges, Melsungen, Fed. Rep. of Germany

[73] Assignee: Intermedicat GmbH, Emmenbrucke, Switzerland

[21] Appl. No.: 372,740

[22] Filed: Apr. 28, 1982

[30] Foreign Application Priority Data

Aug. 7, 1981 [DE] Fed. Rep. of Germany ....... 3131378

[51] Int. Cl.³ ............................................. A61M 1/00
[52] U.S. Cl. ..................................... 604/322; 285/331
[58] Field of Search ....................... 128/760; 285/331; 604/317, 322, 323, 325, 326, 327

[56] References Cited

U.S. PATENT DOCUMENTS

| 793,869 | 7/1905 | Anderson | 285/331 |
| 3,529,599 | 9/1970 | Folkman et al. | 604/323 |
| 3,800,795 | 4/1974 | Walker | 604/323 |
| 4,178,934 | 12/1979 | Forman | 604/322 |

FOREIGN PATENT DOCUMENTS 2900806 7/1980 Fed. Rep. of Germany .

Primary Examiner—Stephen C. Pellegrino
Assistant Examiner—J. L. Kruter
Attorney, Agent, or Firm—Marshall, O'Toole, Gerstein, Murray & Bicknell

[57] ABSTRACT

A secretion collecting device consists of a rigid holder, from which a bag is suspended. A secretion drainage tube running from the patient is connected to a pipe on the holder. The bag has a tube one end of which enters the interior space of the bag and the other end of which projects from the bag and is pushed telescopically onto the lower end of the pipe. The bag tube can slide with respect to the pipe so that the connection adjusts to shifts and deformations of the bag without becoming loose or separating.

9 Claims, 10 Drawing Figures

BODY SECRETION COLLECTING DEVICE WITH IMPROVED LIQUID CONDUIT CONNECTION BETWEEN CONTAINER AND HOLDER

This invention is concerned with a liquid secretion collecting device having a holder and a container to be suspended from the holder, said container having a liquid feed line which is sealably connectible to the end of a pipe or connecting nipple on the holder

BACKGROUND OF THE INVENTION

In a previously known liquid secretion collecting device (DE-AS No. 29 00 806), a flexible bag is provided which is fastened by a loop to a hook on a rigid holder. The holder has a downwardly directed rigid channel to which is fastened the inlet end of a tube that leads into the secretion bag and which is rigidly connected to the secretion bag. For this purpose, the end pieces of the holder channel and of the bag tube are provided with engaging conical parts which are pushed into one another under pressure. However, this type of conduit coupling having mating conical connecting parts has a disadvantage in that a seal at the joint is only guaranteed when the two line portions joined together are not pulled apart in the longitudinal direction. A slight shift in longitudinal direction of one of the conical connecting parts can cause leakage. As a result, there is a possible danger in that the body secretion can leak out the joint or that air will enter the bag. If that happens and the connecting elements are pressed together again, air pockets may form in the bag and make more difficult subsequent inflow of secretions into the bag.

Furthermore, screw-type connections and bayonet interlocking mechanisms have been known for joining secretion lines together. The respective connecting elements, however, are expensive to manufacture. Upon usage, undesirable twisting of the connected lines takes place during the coupling process.

In secretion collecting devices the container normally consists of a flexible bag, the film walls of which are pulled downwardly with increasing filling. Upon rigid coupling of the feed line, which is connected to the bag, to the holder channel, the bag feed line is exposed to tensile stress which is transferred to the coupling device.

This invention has as an object the provision of a secretion collecting device of the above-mentioned type which permits a shift or movement of the feed conduit or line relative to the holder channel without leakage problems and without application of major tension to the lines or connection.

SUMMARY OF THE INVENTION

In order to solve the described problem, according to the invention the bag tube or feed line and the holder pipe or channel are designed in their connecting areas so that they unite telescopically in the longitudinal direction relative to one another, thereby producing and maintaining a tight seal.

In the secretion collecting device according to the invention the bag tube can shift with respect to the holder pipe or connecting nipple within relatively wide limits without causing leakage problems. Due to the telescopic connection between the bag tube or feed line and the holder pipe or channel, the length of the connecting device can adjust automatically to the respective conditions, in particular, when after fastening the bag to the holder, the position or the shape of the bag is changed. As a rule, a bag of flexible film or sheet material is used as the secretion collecting container.

In a particularly suitable embodiment of the invention, the collecting bag feed line is a flexible tube that surrounds the holder channel which is designed as a rigid pipe or nipple. The flexible tube adjusts to all position and shape changes of the bag relative to the holder. Since the holder channel is designed as a rigid pipe, the coupling location is always fixed relative to the bag holder. It is important that the distance to which the tube is pushed onto the holder pipe be sufficiently long to permit a longitudinal movement of the tube on the pipe to accommodate shifting of the bag, or deformation of the bag as filling increases, to the extent necessary to keep the tube telescoped on the holder pipe while permitting the tube to move or slide on the pipe.

In an especially advantageous embodiment of the invention, the holder pipe has at least one circumferential annular thickened portion or protrusion in the area telescopically covered by the bag tube. By this means an adequate seal at the connecting location is guaranteed. Also, upon pushing the bag tube onto the holder pipe, the friction is substantially independent of the pushing force so that the friction is mainly determined by the protrusion shape and size.

Another suitable embodiment of the invention provides that the area of the holder pipe to which the bag tube is fastened be surrounded by a guard that extends over the pipe lower end and is spaced radially from the pipe. The guard provides mechanical protection for the connecting site so that the tube cannot be unintentionally pulled off the pipe or otherwise be separated. Furthermore, the guard improves the protection against contamination.

Suitably the pipe and the guard are formed in one piece or integrally with the holder so that there is no need for separate connecting elements.

DETAILED DESCRIPTION OF THE DRAWINGS

Figure 1:
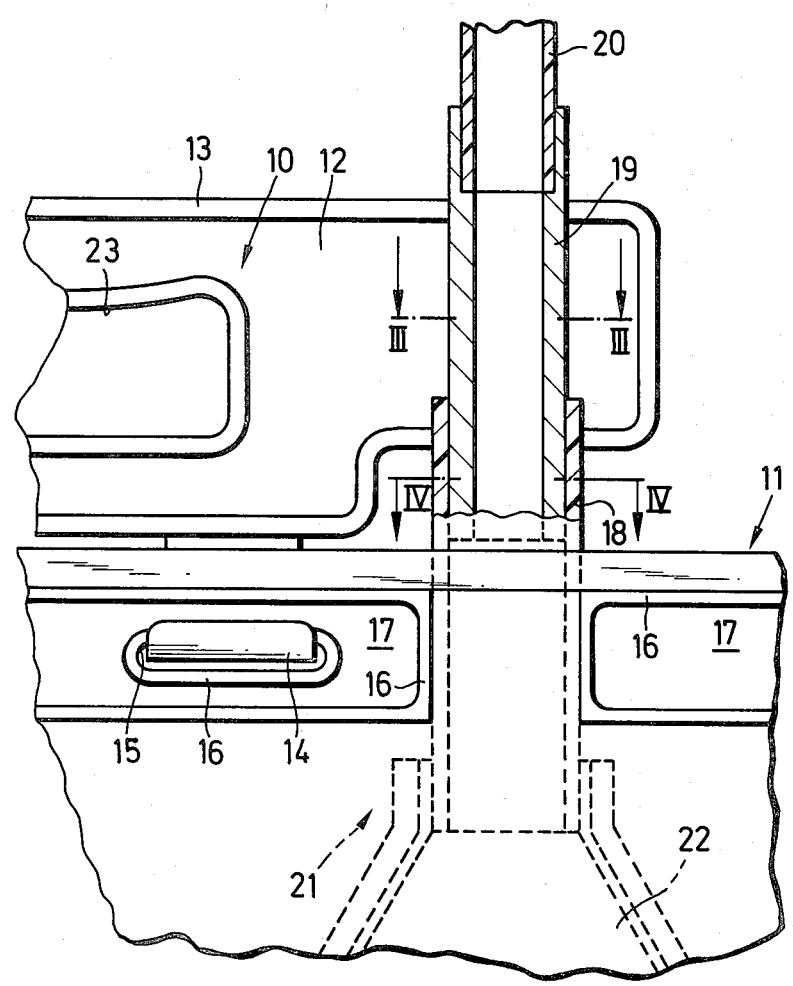
FIG. 1 is an elevational view, partially in section, showing a secretion collecting bag suspended from one embodiment of bag holder according to the invention.

The secretion (urine) collecting device illustrated in FIG. 1 consists of a plate-shaped bag holder 10 and a bag 11 to be suspended on the holder 10, said bag being of flexible thin sheet or film material. The holder 10 has a flat or planar area 12 with a peripheral thickened rib or rim 13. Tabs 14 project downwardly from the lower rim of the plate 12. The lower ends of said tabs 14 are bent like hooks so that the eyes 15 in bag 11 can be placed on them so as to suspend bag 11 from the holder 10.

The bag 11 is made of two flexible sheets joined together along their upper edges by sealing seams 16. The sealing seams 16 run parallel along the upper end of bag 11 and surround the longitudinal areas 17 where the eyes 15, also defined by sealing seams 16, are located.

The bag 11 is tightly joined to vertical tube 18 which projects into the bag interior. Tube 18 sealingly passes between the two sheets of the bag and extends upwardly above the bag upper edge.

The holder 10 has a vertical cylindrical pipe 19 which is integrally formed therewith as one piece. The upper end of pipe 19 is adapted to receive the end of a secretion drainage tube 20 and to be fastened thereto. The end of the drainage tube 20 is spaced away from the patient. The lower end of rigid pipe 19 extends beyond the plate 12 and the rim 13 and therefore projects freely downwardly, that is, its cylindrical lower end does not come into contact with any part of holder 10. The upper end of the cylindrical tube 18 is pushed over the lower end of the pipe 19 so that the tube 18 telescopically surrounds the tube 19 in super-imposed position. The inner diameter of the tube 18 is so adjusted to the outer diameter of the pipe 19 that the inner space of the tube 19 and the tube 18 are sealed against entry of outside air. Nevertheless, the tube 18 can slide longitudinally on pipe 19.

The lower end of tube 18, in the interior hollow space 21 of bag 11, extends a distance beyond the lower sealing seam 16. A film valve 22 is attached at the lower end of the tube 18. The upper edge of film valve 22 extends around the lower end of tube 18. The valve has two flat adjoining film portions, between which liquid secretions flow from the tube 18. The film valve 22 prevents reverse flow of liquid from the hollow space 21 into the tube 18.

In a known manner, an air valve (not illustrated) can be provided at the holder 10, at the bag 11, or within the secretion drainage tube 20.

The holder 10 has a finger gripping opening 23 in the plate 12 so that the holder 10, together with the bag 11 suspended from it, can be transported. When in use, the holder 10 is either fastened on the bed of the patient or on a suspension device.

While in the embodiment illustrated by FIG. 1 the pipe 19 has a continuous cylindrical outer surface, in the FIGS. 2a to d, various types of embodiments of the pipe are illustrated where the pipe has, in the lower area, a circumferential bulge or protrusion over which the tube 18 is telescopically pushed and forms, in cooperation with the tube 18, a localized sealing area. The embodiment of FIG. 2a, the pipe 191, in the proximity of its lower end, is provided with a circumferential bulge 24 the lower defining rim 25 of which extends in a cone shape to the lower edge of the pipe 191. The wall thickness of the pipe 191, at the lower edge, is smaller than in the tube area above bulge 24. The pushing-on of tube 18 is facilitated in this manner.

Figure 2A:
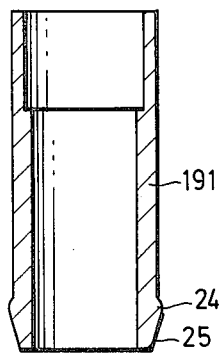
FIGS. 2a to 2d are sectional views of various embodiments of connecting pipes which can be provided on the bag holder.
Figure 2B:
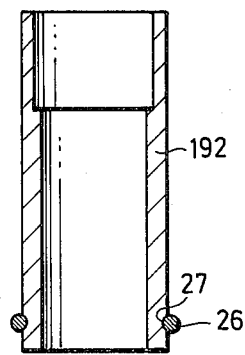

According to FIG. 2b the pipe 192 has an O-ring 26 which is inserted in a circular groove 27, having a partially circumferential cross-section, on the lower end of the pipe 192. After pushing flexible tube 18 on the pipe 192 the O-ring provides the main seal since the tube 18 becomes radially enlarged over the O-ring 26. Once the tube end is pushed over the O-ring 26, the end of tube 18 contacts the outer surface of pipe 192.

Figure 2C:
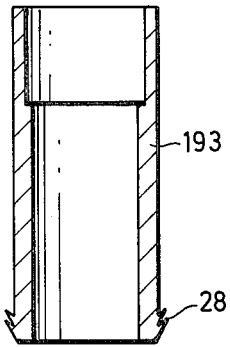

FIG. 2c shows a pipe 193 which has circumferential saw-tooth shaped teeth 28 around its lower end. The teeth 28 permit sliding of tube 18 onto pipe 193, however, they render difficult sliding the tube in the opposite or downward direction.

Figure 2D:
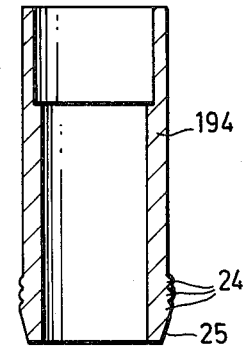

In the embodiment shown in FIG. 2d several annular bulges or ridges 24 are arranged in close sequence one behind the other on the lower end of pipe 194. The lowermost annular bulge 24 merges into a conical area 25 as has already been described in conjunction with FIG. 2a.

Figure 5:
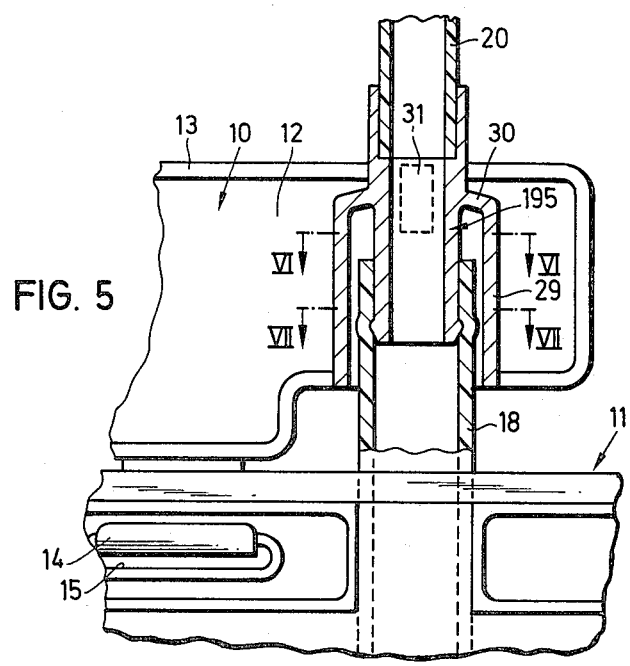
FIG. 5 is a view similar to FIG. 1 but shows a second embodiment of a bag holder with a connecting pipe thereon having a guard or shield over the pipe lower portion.

In the embodiment shown in FIG. 5, the same bag 11 is used as in the embodiment shown in FIG. 1. The holder 10, as well, corresponds substantially to that of FIG. 1. The characteristic distinguishing the two embodiments is that in the secretion collecting device of FIG. 5 the pipe 195, over a portion of its length, is surrounded by a guard or cover 29 in the form of a shell which extends past the lower end of pipe 195. The guard 29 has a substantially U-shaped cross-section and the ends of its sidewalls extend vertically against the plate 12 and merge integrally into it. The inner surface of the guard 29 is spaced outwardly from the outer surface of pipe 195 so that around the lower portion of the pipe 195, a space is provided which is only open downwardly to permit sliding tube 18 onto the pipe. The upper end of the guard 29 is coverably connected to pipe 195 by annular wall 30.

Figure 3:
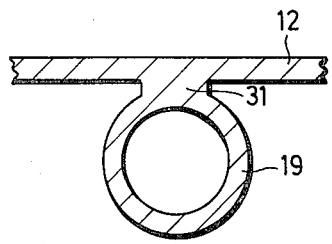
FIG. 3 is a sectional view taken along the line III—III of FIG. 1.
Figure 4:
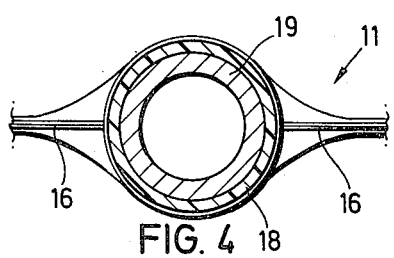
FIG. 4 is a sectional view taken along the line IV—IV of FIG. 1.
Figures 6, 7:
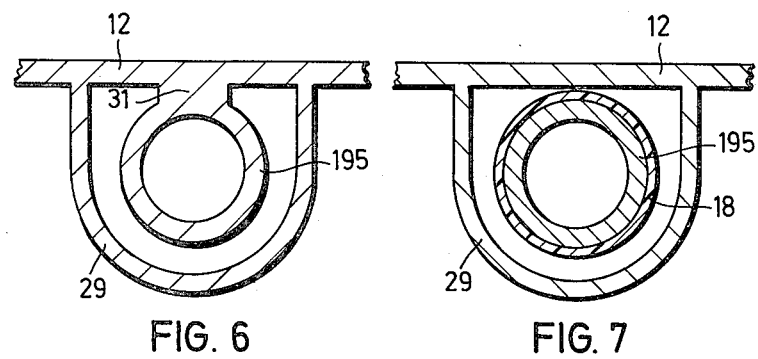
FIG. 6 is a sectional view taken along the line VI—VI of FIG. 5.
FIG. 7 is a sectional view taken along the line VII—VII of FIG. 5.

In the above-described embodiments, the pipe is made with the holder in one piece. It is made of a synthetic polymeric material. The site at which the wall of the pipe is connected to the holder 10 is located above that area onto which the tube 18 is pushed or slid upwardly. This connecting site is identified by number 31 in FIGS. 3 and 5.

What is claimed is:

1. A body liquid secretion collecting device comprising:
    a secretion collecting container holder means from which a secretion collecting container means is suspended having a rigid holder pipe fixedly joined thereto, the pipe having a lower end of constant outer diameter and an exposed upper end, the pipe being integrally formed vertically on a front face of the holder means and forming a single unit with said holder and with said pipe lower end having a substantially cylindrical outer surface; and
    a secretion collecting container means, adapted to be movably and replaceably directly suspended from the holder means, having a cylindrical tube means fixedly joined to the container means with an end in the container and with an inlet end, extending out of the container means, having a substantially constant inner diameter such that it is fluid sealably connectible telescopically to the holder pipe lower end and movable longitudinally while the tube inlet end inner surface maintains sealing contact with the essentially cylindrical outer surface of the pipe lower end thereby maintaining the fluid seal during vertical movement and displacement of the bag while being filled with body liquids, and with the tube and the pipe being sealed together against the entry of outside air.

2. A body liquid secretion collecting device according to claim 1 or 3 in which the pipe upper end is connectible to a secretion drainage tube leading away from a patient.

3. A body liquid secretion collecting device according to claim 1 in which the tube is a flexible tube which can slidably telescope around the pipe lower end.

4. A body liquid secretion collecting device according to claim 1 or 3 in which the pipe lower end has an annular ridge in the area adapted to be covered by the container means feed tube inlet end.

5. A body secretion collecting device according to claim 1 in which the container tube inlet end and the pipe lower end are substantially axially aligned when joined together.

6. A body liquid secretion collecting device according to claim 1 or 3 including a stationary guard in the form of a shell, surrounding and spaced outwardly from the lower end of the pipe, adapted to surround the container means tube inlet end with the tube inlet end out of radial contact with the guard inner surface.

7. A body liquid secretion collecting device according to claim 1 or 3 in which the pipe is integral with the holder along the back of the pipe.

8. A body liquid secretion collecting device according to claim 1 or 3 including a stationary guard in the form of a shell, surrounding and spaced outwardly from the lower end of the pipe, adapted to surround the container means tube inlet end with the tube inlet end out of radial contact with the guard inner surface, and with the guard integral with the holder.

9. A body liquid secretion collecting device according to claim 1 or 3 in which the secretion collecting container means is a flexible bag and the tube inlet end has a length long enough to remain in sealable telescoping engagement with the pipe lower end even when the bag fills with liquid and tension is thereby applied to the tube which may result in it sliding axially downwardly, in a direction off of the pipe, for a distance less than the length of the tube inlet end originally telescoped onto the pipe.

* * * * *